United States Patent [19]

Rosenberg et al.

[11] Patent Number: 5,720,973
[45] Date of Patent: Feb. 24, 1998

[54] PREPARATION OF COLLOIDAL AQUEOUS SOLUTIONS OF ACTIVE SUBSTANCES OF LOW SOLUBILITY AND A LIPID THEREFOR

[75] Inventors: Joerg Rosenberg, Ellerstadt, Germany; Cynthia Romerdahl, Wayland, Mass.; Hans-Heinrich Gruenhagen, Ludwigshafen, Germany

[73] Assignee: Knoll Aktiengesellschaft, Ludwigshafen, Germany

[21] Appl. No.: 492,006

[22] PCT Filed: Feb. 7, 1993

[86] PCT No.: PCT/EP94/00333

§ 371 Date: Jul. 19, 1995

§ 102(e) Date: Jul. 19, 1995

[87] PCT Pub. No.: WO94/19019

PCT Pub. Date: Sep. 1, 1994

[30] Foreign Application Priority Data

Feb. 18, 1993 [DE] Germany ............ 43 05 004.2

[51] Int. Cl.$^6$ ............................................. A61K 9/127
[52] U.S. Cl. ............................... 424/450; 264/4.1
[58] Field of Search ............................ 424/450; 264/4.1, 264/4.3, 4.4, 4.6; 428/402.2

[56] References Cited

U.S. PATENT DOCUMENTS 3,960,935  6/1976  Samour ............................ 260/485 G
4,619,794  10/1986  Hauser ............................ 264/4.1

FOREIGN PATENT DOCUMENTS 317 120    5/1989   European Pat. Off. .
366 990    5/1990   European Pat. Off. .
456 106    11/1991  European Pat. Off. .
30 10 041  10/1981  Germany .
40 02 165  8/1991   Germany .

OTHER PUBLICATIONS

Voigt: Lehrbuch der Pharm. Tech. Tech. 5th Ed. Verlag Chemie p. 334, 1984.
Pharm. Techn. Intern., Feb. 1991, p. 15J.
J. Pharm. Sci. 72 (1983) 1014.

Primary Examiner—Gollamudi S. Kishore
Attorney, Agent, or Firm—Keil & Weinkauf

[57] ABSTRACT

A process for producing solutions of active substances of low solubility, which comprises (1) dissolving the active substance with a phospholipid and a water-soluble lipid in an organic solvent, (2) evaporating the resulting solution to dryness, (3) taking up the residue in a strongly acidic buffer and stirring at elevated temperature until a colloidal solution is produced, (4) cooling the colloidal solution and adjusting to a pH of 6–7 and sterilizing. Particularly suitable for the process are lipids of the formula

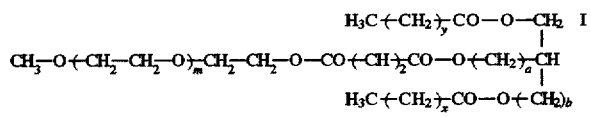

wherein m, a, b, x and y have the meanings indicated in the description.

2 Claims, No Drawings

PREPARATION OF COLLOIDAL AQUEOUS SOLUTIONS OF ACTIVE SUBSTANCES OF LOW SOLUBILITY AND A LIPID THEREFOR

This application is a 371 of PCT/EP94/00333 filed Feb. 7, 1993.

The administration of a medicinal substance by, for example, injection or infusion into the blood stream is often prevented by its low solubility in aqueous systems. This is why in recent years various processes have been developed for formulating, with the aid of suitable solubilizers, the medicinal substance in an aqueous phase.

Most of these processes make use of the solubilizing effect of detergents or emulsifiers (cf. Voigt: Lehrbuch der pharmazeutischen Technologie 5th Edition, Verlag Chemie, p. 334). Although the preparation of such solutions is very straightforward, and a large number of medicinal substances can be solubilized thereby, the toxicity deriving from the detergents often causes considerable problems.

Another possibility is to mix the medicinal substances with the aid of cyclic carbohydrates (cyclodextrins) which complex the medicinal substance (Pharm. Techn. Intern., February 1991, p. 15) and thus often crucially improve the solubility. However, since the internal cavity of the cyclodextrins is limited, many molecules cannot be complexed for steric reasons although the cyclodextrins are to be regarded as more toxicologically favorable than the detergents.

Another suitable class of solubilizers comprises the phospholipids which, as endogenous molecules (they are a constituent of every cell membrane), show very good tolerability even in injection solutions. However, the use of phospholipids often fails because in aqueous systems they form not molecular solutions but only colloidal aggregates. However, on simple dispersion of phospholipids in aqueous solutions these colloid particles are so large that such phospholipid-containing solutions generally cannot be used for formulations for injection and infusion (risk of embolism). The coarsely colloidal cloudy solutions obtainable by suspending phospholipids in aqueous systems must therefore first be homogenized by suitable methods before use thereof so that the size of the particles in the solutions is reduced to values permitting use of the phospholipids in solutions for injection or infusion (cf. U.S. Pat. No. 5,008,050). Only in very few cases is it possible with selected medicinal substances to obtain injectable medicinal substance formulations direct from active substance and phospholipid in aqueous systems without it first being necessary to reduce the size of the colloidal particles by relatively elaborate homogenization methods.

Most of all known pharmaceutical active substances are weakly basic, ie. have an amino group which can be protonated. Such weakly basic substances often have sufficient solubility in water by forming salts with suitable organic or inorganic acids. However, the salts generally have adequate solubility only in the acidic medium. pH values of this type are unacceptable for pharmaceutical formulations for injection. On attempting to adjust to neutral pH values, the active substances precipitate to a considerable extent so that usually only relatively low concentrations can be obtained at physiological pH values, or recourse must be had to cosolvents from which, however, the active substances likewise often precipitate again after injection (J. Pharm. Sci. 72 (1983) 1014).

The present invention relates to a process for producing solutions of active substances of low solubility, which comprises 1. dissolving the active substance with a phospholipid and a water-soluble lipid in an organic solvent,
2. evaporating the resulting solution to dryness,
3. taking up the residue in a strongly acidic buffer and stirring at elevated temperature until a colloidal solution is produced,
4. cooling the colloidal solution and adjusting to a pH of 6–7 and sterilizing.

Particularly suitable active substances for the novel process are those which normally have a low solubility in water but dissolve in the presence of acids. Examples of substances of this type are, in particular, active substances with amino groups which can be protonated in the molecule, ie. all basic medicinal substances whose solubility in demineralized water, even in the form of the salts, is on average below 1 mg/ml.

If the intention is to produce solutions of active substances which have low solubility and do not even dissolve in acids, it is necessary to increase the proportion of water-soluble lipid in relation to the phospholipid.

It is possible to use as phospholipid component all natural or synthetic phospholipids; mixtures of different phospholipids are also possible. The lecithins isolated from egg yolk or soybean are particularly preferred, especially when they contain more than about 80 % phosphatidylcholine.

Water-soluble lipids which can be used are lipids conventionally used in pharmaceuticals. These include, in particular, the following substances listed in the pharmacopeias: fatty acid salts (sodium stearate/palmitate); partial glycerides (glycerol monostearate/oleate, acetylated monoglycerides); sugar esters (sorbitan monolaurate/oleate/palmitate/stearate/tristearate); salts of sulfonic acids (sodium cetylstearyl sulfate/lauryl sulfate/tetradecyl sulfate); ethoxylates of fatty acids/glycerides/sugar esters (macrogol stearate 400, polyoxyl 40/50 stearate, polyoxyl 10 oleyl ether, polyoxyl 20 cetostearyl ether, polydocanol 600, macrogol glycerol hydroxystearate, macrogol 1000 glycerol monolaurate/oleate/stearate/triricinoleate, polysorbate 20/40/60/80; and poloxamers.

A novel synthetic water-soluble lipid of the formula I has proven to be very suitable besides these, especially for producing solutions of the bisnaphthalimides of U.S. Pat. No. 4 874 683.

The phospholipid:water-soluble lipid ratio in the formulations can be from 10:1 to 1:1 by weight. The ratio which is most suitable for the particular active substance must be determined empirically.

To adjust the pH values and keep them constant the solution must contain a suitable buffer substance. Particularly preferred for this purpose is phosphoric acid because this permits stable adjustment of the necessary very low initial pH values.

It has emerged that initial pH values below 2 are to be preferred for the success of the preparations by the process according to the invention. Thus, suitable buffer substances are those able to adjust to these acidic pH values. The buffer used ought simultaneously to have a sufficient buffer capacity also in the physiological pH range between pH 6 and 7 in order, after titration of the solution, to keep the pH constant in this pH range without fluctuations. Phosphoric acid solutions in a concentration of about 0.05 to 0.15 mol/l have proven very suitable. A phosphoric acid concentration of 0.14 mol/l is particularly beneficial. Solutions of this type as a rule have a pH in the optimal region of about pH 1.5 and, in the subsequent titration with dilute sodium hydroxide solution, afford pH-stable solutions in the physiological pH region of about pH 7, which are moreover usually isotonic with blood (about 280 mosmol/kg) so that further isotonicization of the solutions is unnecessary.

The substances of low solubility are mixed with a phospholipid and the water-soluble lipid in strongly acidic aqueous solution. Simple stirring is sufficient to dissolve or emulsify the substances without the need to use a special homogenization method. A stable solution or emulsion of the active substance is obtained after adjustment of the pH to 6–7.

A solution of the substance mixture is produced particularly satisfactorily when the mixture is previously mixed together by dissolving in a suitable organic solvent and subsequently removing the solvent completely.

It has emerged in many cases that it is beneficial to allow the solubilization to take place initially in only a small amount of the (strongly acidic) buffer solution (about 10 % of the total buffer solution required). After solubilization and pH titration have taken place, the volume is then made up to the intended final volume.

The evaporation to dryness can take place by distillation or freeze-drying. It is particularly beneficial with small batches to evaporate the solution by rotary evaporation because in this case the substance is obtained in the form of a film on the inside of the evaporator, which facilitates and speeds up the subsequent hydration.

An appropriate amount of the strongly acidic buffer solution is then added to the dry residue, and the mixture is stirred at elevated temperature until a homogeneous colloidal solution which is free of coarse colloidal aggregates has formed. This solution is cooled to room temperature and, while stirring, an aqueous solution of a base is added until a pH of about 6–7 is reached. The finished solution can then be filtered stepwise through membrane filters down to a pore size of 0.2 μm (sterile filtration), ie. sterilized.

As the data in the examples show, the combination of described steps improves the solubility of pharmaceutical active substances of low solubility so greatly that they can be administered in aqueous solutions, which is a great advantage for therapeutic use thereof.

Another advantage of the novel solutions is that the toxicity of the active substances therein is reduced so that the dosage thereof can be increased by up to a factor of 2 without unwanted side effects occurring. This is particularly important for the use of carcinostatics.

Particularly suitable water-soluble lipids for the novel process are those which have the formula I

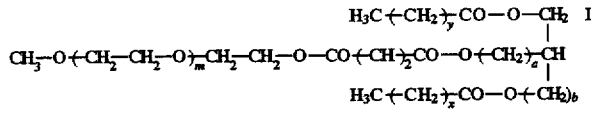

where m is a number from 40 to 500, preferably from 40 to 200, one of the numbers a and b is 0 and the other is 1, x is a number from 10 to 18, preferably 12, 13 or 14, and y is a number from 10 to 18, preferably 12, 13 or 14. Particularly preferred compounds of the formula I are those where x and y are identical and are 12, 13 or 14.

The present invention likewise relates to these lipids. They can be prepared from a compound of the formula

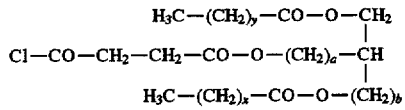

by condensation with a polyethylene glycol monomethyl ether (M=1800–22,000, preferably about 5000) of the formula

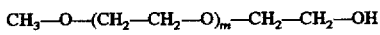

in the presence of a base such as pyridine.

EXAMPLE 1

U.S. Pat. No. 4,874,683 describes active substances which have a bisnaphthalimide structure. Because the solubility in water is very low, it is very difficult to prepare aqueous solutions of active substance with sufficient concentration. Although it is possible with the aid of solubilizers such as dimethyl sulfoxide to prepare solutions for injection, the active substance rapidly flocculates out of these again in the blood after the injection.

The solubility in aqueous formulations was investigated using a derivative of these bisnaphthalimides

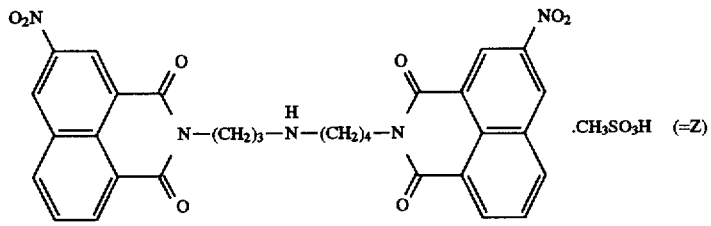

as follows:

Experiment A (Comparative Experiment)

40 mg of Z were dissolved in 10 ml of methylene chloride/methanol (9+1). The solvent was completely removed again from the solution under reduced pressure in a rotary evaporator. 8 ml of a 0.14 molar phosphoric acid solution (pH≈1.5) were added to the residue, and the flask was rotated on the rotary evaporator (without reducing the pressure) at a waterbath temperature of 50° C. for 1 h. It was possible in this way for a considerable part of the active substance to be dissolved. Cooling to room temperature was followed by titration with 2 molar sodium hydroxide solution to a pH of 6.8, and the volume was made up to 10 ml with phosphate buffer pH 6.8. Most of the active substance then precipitated. The clear supernatant was filtered through a 0.2 μm syringe sterile filter, and the active substance concentration in this solution was determined by photometry. The active substance content in this solution was 0.04 mg/ml.

Experiment B (Comparative Experiment)

The experiment was carried out as in Experiment A but 50 mg of the novel water-soluble lipid I-a were weighed in in addition to the active substance. After removal of the solvent, 10 ml of a 0.14 molar phosphoric acid solution which had been titrated with 2 molar sodium hydroxide solution to pH 6.8 were added, and the mixture was likewise stirred in the rotary evaporator waterbath at 50° C. for 1 h.

The active substance content of the titrated solution (0.2 μm filter) was 0.04 mg/ml.

Experiment C (Comparative Experiment)

The experiment was carried out as in Experiment B but 250 mg of phospholipid (egg lecithin E 100 from Lipoid KG, Ludwigshafen) were employed in place of the novel water-soluble lipid I-a.

The active substance content of the filtered solution was 0.04 mg/ml.

Experiment D (Comparative Experiment)

The experiment was carried out as in Experiment A but 50 mg of the water-soluble lipid I-a were weighed in in addition to the active substance.

The active substance content of the filtered solution was 0.08 mg/ml.

Experiment E (Comparative Experiment)

The experiment was carried out as in Experiment B but 250 mg of phospholipid (egg lecithin E 100) were weighed in in addition to the active substance and the water-soluble novel lipid I-a.

The active substance content of the filtered solution was 0.1 mg/ml.

Experiment F (Comparative Experiment)

The experiment was carried out as in Experiment A but 250 mg of phospholipid (egg lecithin E 100) were weighed in in addition to the active substance.

The active substance content of the filtered solution was 2.8 mg/ml.

Experiment G

The experiment was carried out as in Experiment F but 50 mg of the novel water-soluble lipid I-a were additionally weighed in. The filter surface of the sterile filter was free of undissolved residues of active substance in this experiment, in contrast to Examples 1–6.

The active substance content of the filtered solution was 4.0 mg/ml.

The novel water-soluble lipid I-a used for Experiments B, D, E and G was prepared as follows:

35.00 g of polyethylene glycol monomethyl ether (MW about 5000) were dissolved in 70 ml of dichloromethane together with 0.71 ml of pyridine. To this were added with stirring 4.81 g of 1,2-dipalmitoylglycerol 3-(3-chloroformyl)propionate dissolved in 5 ml of dichloromethane. The mixture was refluxed for 48 h and then a further 4.81 g of 1,2-dipalmitoylglycerol 3-(3-chloroformyl) propionate were added. The mixture was refluxed for a further 24 h. The solvent was then removed under reduced pressure, and the residue was stirred with 500 ml of diethyl ether. This suspension was filtered with suction through a wide suction funnel. The residue on the suction funnel was dissolved in 300 ml of dichloromethane and extracted by shaking carefully (emulsion formation) once with 100 ml of hydrochloric acid (1 molar) and twice with 100 ml of water each time. The organic phase was dried with $Na_2SO_4$ and evaporated. 785 ml of ethanol were added to the residue, heating to dissolve, and the mixture was left to crystallize in an ice bath. The precipitate was filtered off with suction, washed with ice-cold ethanol and dried.

Yield: 37.84 g of colorless powder (95 %) Melting range: 55°–59° C.

The following compounds of the formula I were prepared in a similar way.

Ib a=0, b=1, x=y=14, m about 40–45, colorless powder, melting range 50°–52° C., yield 94 %;

Ic a=0, b=1, x=y=12, m about 100–120, colorless powder, melting range 57°–58° C., yield 95 %;

Id a=1, b=0, x=y=14, m about 100–120, colorless powder crystallized from ethyl acetate/diisopropyl ether (4:6), melting range 70°–70° C., yield 81%.

EXAMPLE 2

35 mg of β-carotene were dissolved in a 100 ml round-bottomed flask together with 500 mg of egg lecithin E 100 (Lipold KG, Ludwigshafen) and 500 mg of Cremophor RH-40® (BASF) in a mixture of 30 ml of cyclohexane and 5 ml of methanol. The solvent was then completely removed in a rotary evaporator under reduced pressure so that a thin red film remained on the wall of the glass flask. 18.5 ml of a 0.14 molar phosphoric acid solution (pH ⁻1.5) were added to this residue. The flask was then rotated at a waterbath temperature of 50° C. until the entire film had dissolved off the glass wall (15 min). This solution was titrated while stirring at room temperature with 2 molar sodium hydroxide solution to pH 7. The active substance content was 1.70 mg/ml. It was possible to sterilize the solution by stepwise filtration through 1.2 μm, 0.45 μm and 0.2 μm filters.

When Example 2 was carried out as in Example 1, Experiments A, B, C, D, E and F, the active substance content of the solution was less than 0.25 mg/ml.

We claim:

1. A process for producing a pharmaceutical preparation of an active substance of low solubility, 1. dissolving the active substance with a phospholipid and a water-soluble lipid of the formula I $$\begin{array}{c} H_3C+CH_2\rangle_y CO-O-CH_2 \\ | \\ CH_3-O+CH_2-CH_2-O\rangle_m CH_2-CH_2-O-CO+CH\rangle_2 CO-O+CH_2\rangle_a CH \\ | \\ H_3C+CH_2\rangle_x CO-O+CH_2)_b \end{array} \quad I$$

where m is a number from 40 to 500, a and b are either 0 or 1; when one of either a or b is 0, the other is 1; x is from 10 to 18; and y is from 10 to 18;

in an organic solvent until a solution is formed, 2. evaporating the solution to dryness until a residue is formed, 3. taking up the residue in an acidic buffer having a pH of 2 or less, and stirring the buffer at a temperature, of about 50° C. until a colloid is formed, and 4. cooling the colloid to about room temperature, adjusting to a pH of 6–7 and sterilizing.

2. A process as defined in claim 1, wherein the ratio of phospholipid to water-soluble lipid is from 10:1 to 1:1 by weight.

* * * * *

UNITED STATES PATENT AND TRADEMARK OFFICE
CERTIFICATE OF CORRECTION

PATENT NO.: 5,720,973

DATED: February 24, 1998

INVENTOR(S): ROSENBERG et al.

It is certified that error appears in the above-identified patent and that said Letters Patent is hereby corrected as shown below:

On the cover page, item [22], "Feb. 7, 1993" should be --Feb. 7, 1994--.

Signed and Sealed this

Twenty-eighth Day of April, 1998

Attest:

BRUCE LEHMAN

Attesting Officer     Commissioner of Patents and Trademarks